(12) United States Patent
Erneta et al.

(10) Patent No.: US 8,691,899 B2
(45) Date of Patent: Apr. 8, 2014

(54) ANTIMICROBIAL POLYMER COMPOSITIONS AND THE USE THEREOF

(75) Inventors: Modesto Erneta, Princeton Junction, NJ (US); Joerg Priewe, Kiel (DE)

(73) Assignee: Ethicon, Inc., Somerville, NJ (US)

( * ) Notice: Subject to any disclaimer, the term of this patent is extended or adjusted under 35 U.S.C. 154(b) by 1014 days.

(21) Appl. No.: 11/869,397

(22) Filed: Oct. 9, 2007

(65) Prior Publication Data

US 2009/0092648 A1  Apr. 9, 2009

(51) Int. Cl.
| | | |
|---|---|---|
| A61L 31/06 | (2006.01) | |
| A61K 31/16 | (2006.01) | |
| C08G 63/91 | (2006.01) | |
| C08G 63/08 | (2006.01) | |

(52) U.S. Cl.
USPC ........... 524/217; 523/122; 524/198; 524/199; 525/450; 528/288; 528/354; 424/78.17; 424/423; 424/426; 606/228; 606/230

(58) Field of Classification Search
None
See application file for complete search history.

(56) References Cited

U.S. PATENT DOCUMENTS

| | | | | |
|---|---|---|---|---|
| 2,459,062 | A | * | 1/1949 | Moss et al. .................... 514/625 |
| 2,589,674 | A | * | 3/1952 | Cook et al. ..................... 554/52 |
| 3,388,704 | A | * | 6/1968 | Kurtz .............................. 606/231 |
| 4,268,402 | A | * | 5/1981 | Kurze et al. .................... 442/102 |
| 5,166,297 | A | | 11/1992 | O'Lenick, Jr. et al. |
| 5,237,035 | A | | 8/1993 | O'Lenick, Jr. et al. |
| 5,328,685 | A | | 7/1994 | Janchitraponvej et al. |
| 5,393,491 | A | | 2/1995 | Dassanayake et al. |
| 5,573,726 | A | | 11/1996 | Dassanayake et al. |
| 5,631,005 | A | | 5/1997 | Dassanayake et al. |
| 6,617,142 | B2 | | 9/2003 | Keogh et al. |
| 2004/0033208 | A1 | | 2/2004 | Cagle et al. |
| 2004/0058924 | A1 | | 3/2004 | Schlitzer et al. |
| 2006/0263329 | A1 | * | 11/2006 | Eemeta et al. ............. 424/78.37 |
| 2006/0264347 | A1 | | 11/2006 | Ming et al. |

FOREIGN PATENT DOCUMENTS

| | | | |
|---|---|---|---|
| WO | 98/50087 | | 11/1998 |
| WO | 01/26708 | | 4/2001 |
| WO | WO-02/22923 | * | 3/2002 |
| WO | 2006/125098 | | 11/2006 |

OTHER PUBLICATIONS

Encyclopedia of Polymer Science and Engineering vol. 12; 1989; pp. 118-119.*

* cited by examiner

Primary Examiner — David Buttner
(74) Attorney, Agent, or Firm — Roberts Mlotkowski Safran & Cole, P.C.

(57) ABSTRACT

An antimicrobial composition and a medical device having that antimicrobial composition that includes a complex of an anionic polyester with a monomeric amidoamine having at least one amide group and at least one amine group, wherein the amine group is either a primary amine, or a secondary amine, or a tertiary amine, or a quaternary amine, or a combination thereof and the anionic polyester has at least one carboxylic group.

16 Claims, No Drawings

ANTIMICROBIAL POLYMER COMPOSITIONS AND THE USE THEREOF

FIELD

This disclosure relates to polymer compositions and their use for making or coating articles, such as medical devices. More specifically, antimicrobial compositions are disclosed that are complexes of an anionic polymer with an antimicrobial cationic surfactant. In particular, disclosed herein are complexes of anionic polyesters with aminoamides that may be used alone or in combination with medical devices.

BACKGROUND

In a surgical setting, when a medical device is used, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of surgical site infections is often associated with bacteria that colonize on the medical device. For example, during a surgical procedure, bacteria from the surrounding atmosphere may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial agents into the medical devices. Such devices desirably provide effective levels of antimicrobial agent while the device is being used.

Amidoamines are best known as surface-active agents. They are also known for their ability to serve as core initiators for dendrimer synthesis and for assembly of poly(amidoamine) dendrimers. Amidoamines in their monomeric form can serve as binders or crosslinking reagents that provide reactive groups for attaching biomolecules or other compounds together or to material surfaces.

Amidoamines have been used with silicone polymers for cosmetic or hair conditioning applications. For example, U.S. Pat. No. 5,166,297 proposes a dimethicone copolyol halo ester intermediate which is said to be useful as an intermediate for reaction with amines to prepare silicone based quaternary compounds for cosmetic or hair conditioning applications.

U.S. Pat. No. 5,237,035 proposes silicone phospholipid polymers which are highly lubricious, produce high levels of foam, have low irritation properties and are film formers when applied to hair and skin. The compounds, because they are based upon terminal dimethicone copoylols make flat polymers when phosphated and derivatized. The polymers are said to orientate themselves into planar sheets, silicone on one side of the plane, a fatty portion on the other side in aqueous and other solutions. These flat polymers produce non-occlusive films when applied to hair skin and fiber.

U.S. Pat. No. 5,328,685 proposes a method of imparting improved conditioning properties to hair comprising treating the hair with a clear conditioning composition comprising an amidoamine salt, the amidoamine salt comprising an amidoamine compound and a silicone compound having at least one quaternary ammonium moiety.

Monomeric amidoamines, in particular myristamidopropyl dimethylamine (MAPD), are also known to have significant antifungal and antiamoebal activity. MAPD is a cationic oil-in-water emulsifier which is often used as a conditioner or a thickener. MAPD is currently used in ophthalmic compositions as a disinfecting and as a contact lens washing solution agent, preservative and surface active agent. In this regard, U.S. Pat. No. 5,393,491 proposes the use of certain amidoamines for disinfecting and cleaning contact lenses and preserving ophthalmic products, and associated ophthalmic compositions are described. U.S. Pat. Nos. 5,573,726 and 5,631,005 each also propose the use of certain amidoamines to disinfect contact lenses and preserve ophthalmic compositions. Ophthalmic compositions containing such compounds are also proposed. The amidoamines proposed are said to possess potent antibacterial and antifungal activity and are chemically compatible with inorganic ions and other materials utilized in ophthalmic compositions.

U.S. Pat. No. 6,617,142 proposes methods for forming a coating of an immobilized biomolecule on a surface of a medical device to impart improved biocompatibility for contacting tissue and bodily fluids. A biomolecule such as a glycoprotein having an unsubstituted amide moiety is proposed for combination with an amine forming agent to form an amine-functional biomolecule. The amine-functional biomolecule is combined with a medical device surface having a chemical moiety such as aldehyde, epoxide, isocyanate, 1,2-dicarbonyl, phosphate, sulfate or carboxylate to form a chemical bond immobilizing the biomolecule on the surface. The chemical bond may be combined with a reducing agent or a stabilizing agent. The aldehyde moiety may be formed by combining a periodate with a 2-aminoalcohol moiety or a 1,2-dihydroxy moiety. Also proposed is an amine-functional medical device surface combined with a biomolecule having a chemical moiety that reacts with an amine moiety. In one form, the amine-functional biomolecule is converted to a guanidino-functional biomolecule and is combined with a medical device surface having a chemical moiety that reacts with a guanidino moiety. In another form, the amine-functional medical device surface is converted to a guanidino-functional surface and is combined with a biomolecule having the chemical moiety.

The general use of amidoamines in treating or preventing infections caused by fungi or acanthamoeba is proposed in U.S. Patent Publication No. 2004/0058924. The amidoamines are said to be highly effective against both acanthamoeba and fungi and less toxic to delicate tissues that may become infected with these types of microorganisms, such as the cornea.

U.S. Patent Publication No. 2004/0033208 proposes antimicrobial compositions containing one or more topically active antibiotics, such as natamycin, and one or more amidoamines. The amidoamines are said to enhance or supplement the antimicrobial activity of natamycin or other topically active antibiotics. The compositions are said to be useful in treating or preventing fungal infections of the eye, ear, nose and throat, as well as sterilizing those tissues prior to surgery or other medical procedures.

WO9850087 proposes coated medical devices adapted to pass through narrow body openings such as catheters. The coatings provided impart durability to the catheter without appreciably adding to the thickness of the catheter and without decreasing the hoop tensile strength of the catheter. The use of amidoamine (EpiCure 3005) to prepare polymeric coatings with an epoxy resin is also proposed.

WO0126708 proposes polymeric valves, valve devices, machines and instruments. The proposed devices include implantable devices with a sufficiently long lifetime that are responsive to the patient's therapeutic requirements and deliver a certain amount of a drug in response to a biological stimulus. Also proposed are methods and processes using a reservoir implant with a valve, whereby a polymeric dendrimeric poly(amidoamine) could be placed into a gel.

Despite these advances in the art, it would be beneficial to incorporate an antimicrobial cationic surfactant into an invasive or implantable medical device to reduce the risk of infection. Further, it would be desirable to provide an antimicrobial composition where the release mechanism into the target environment is independent of the solubilization of the antimicrobial composition in the target environment, and that exhibits immediate activity upon contact with fluids in the human body.

SUMMARY

In one aspect, provided is an antimicrobial composition. The antimicrobial composition includes a complex of an anionic polyester with a monomeric amidoamine having at least one amide group and at least one amine group, wherein the amine group is either a primary amine, a secondary amine, a tertiary amine, a quaternary amine, or a combination thereof and the anionic polyester is selected from the group consisting of an anionic polyester having at least one carboxylic group, a sulfonic acid polymer, and a phosphoric acid polymer.

In another aspect, provided is a method of making a complex of an anionic polyester with antimicrobial cationic surfactant that includes a monomeric amidoamine having at least one amide group and at least one amine group, wherein the amine group is either a primary amine, or a secondary amine, or a tertiary amine, or a quaternary amine, or a combination thereof and the anionic polyester has at least one carboxylic acid group. The method includes the step of incorporating an effective amount of the antimicrobial cationic surfactant with the anionic polyester having least one carboxylic acid group in an aqueous soluble alcohol.

In yet another aspect, provided is a medical device having an antimicrobial composition. The medical device includes a complex of an anionic polyester with an antimicrobial cationic surfactant that comprises a monomeric amidoamine having at least one amide group and at least one amine group, wherein the amine group is either a primary amine, or a secondary amine, or a tertiary amine, or a quaternary amine, or a combination thereof and the anionic polyester has at least one carboxylic acid group.

In still yet another aspect, provided is an antimicrobial composition of an absorbable anionic polyester and an organic cation. The antimicrobial composition includes:

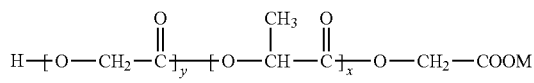

wherein:
x+y ranges from about 5 to about 300 and
M comprises:

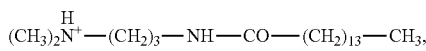

or

In one form, described herein is an antimicrobial composition comprising a complex of an anionic polyester with a cationic surfactant derived from the condensation of fatty acids and esterified dibasic amino acids, wherein the anionic polyester has at least one carboxylic acid group and the formula:

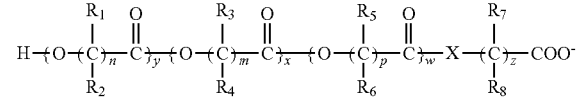

where $800 \geq x+y+w \geq 5$; $y \geq 0$; $x \geq 0$; $w \geq 0$; n, m, p and z independently range from about 1 to about 12; $R_1, R_2, R_3, R_4, R_5, R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

In another form, described herein is an antimicrobial composition comprising a complex of an anionic polyester with an antimicrobial cationic surfactant, wherein the anionic polyester has the formula:

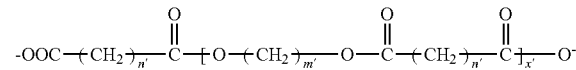

wherein $1 \geq n' \leq 13$; $1 \geq m' \leq 9$; and x' is the degree of polymerization and ranges from about 4 to about 50.

In yet another form, the aminoamides include at least one amide group and at least one amine group, wherein the amine groups are either a primary amine, or a secondary amine, or a tertiary amine, or a quaternary amine or combinations thereof, wherein the primary, secondary or tertiary amines may be rendered into organic cations by protonation, as for example when reacted with an acidic anionic polyester.

In yet still another form, the antimicrobial composition includes a complex of an anionic polyester with an antibacterial amidoamine, wherein the amidoamine comprises:

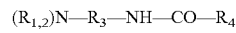

wherein:
$R_1$=H, Alkyl, Aryl, HO—(CH$_2$CH$_2$—O—)$_n$—, MeO—(CH$_2$CH$_2$—O—)$_n$—, HO—(CH$_2$)n-;
$R_2$=H, Alkyl, Aryl, HO—(CH$_2$CH$_2$—O—)$_n$—, MeO—(CH$_2$CH$_2$—O—)$_n$—, HO—(CH$_2$)n-;
$R_3$=alkylene, arylene, —(CH$_2$CH$_{22}$—O—)—(CH$_2$—)$_n$;
$R_4$=Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30;
or the organic cation comprises:

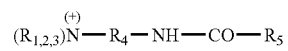

wherein:
$R_1$=H, Alkyl, Aryl, HO—(CH$_2$CH$_2$—O—)$_n$—, MeO—(CH$_2$CH$_2$—O—)$_n$—, HO—(CH$_2$)n-;
$R_2$=H, Alkyl, Aryl, HO—(CH$_2$CH$_2$—O—)$_n$—, MeO—(CH$_2$CH$_2$—O—)$_n$—, HO—(CH$_2$)n-;
$R_3$=H, Alkyl, Aryl;
$R_4$=alkylene, arylene, —(CH$_2$CH$^2$—O—)—(CH$^2$—)$_n$;
$R_5$=H, Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30.

DETAILED DESCRIPTION

Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "complex" refers to an intimate mixture at the molecular scale, preferably with ionic or covalent bonding between the antimicrobial cationic surfactant and the anionic polymer. The complex preferably comprises a salt formed between the anionic polymer and the antimicrobial cationic surfactant, but it may also comprise clusters and/or colloidals of the antimicrobial cationic surfactant.

As used herein, the terms "incorporate", "incorporated", or "incorporating" refer to combining the antimicrobial cationic surfactant with the anionic polyester by physical or chemical means.

Disclosed herein is an antimicrobial composition comprising a complex of an anionic polymer with an antimicrobial cationic surfactant. In one form, the antimicrobial composition comprises a complex of an anionic polyester with an antimicrobial cationic surfactant, wherein the anionic polyester has at least one carboxylic acid group that may be linear or branched. The complex typically comprises from about 5 wt. % to about 75wt. % of the antimicrobial cationic surfactant.

The anionic polymer described herein may be an anionic polyester having at least one carboxylic acid group that may be linear or branched; a sulfonic acid polymer; or a phosphoric acid polymer and the like.

The anionic polyester may be absorbable or nonabsorbable, and may be synthesized via ring opening polymerization of aliphatic lactone monomers. Specifically, the aliphatic lactone monomers are polymerized in the presence of an organometallic catalyst and an initiator. Alternatively, the anionic polyester may be synthesized by condensation polymerization of a diol with diacid, wherein the molar ratio of the diol to the diacid is less than 1. Alternatively, the anionic polyester may be a synthesized anionic form of the reaction product of (a) a polyglycolic acid composition and (b) a polyester of diglycolic acid and a unhindered glycol, as described in more detail in U.S. Pat. Nos. 4,122,129 and 4,095,600, the content each of which is incorporated by reference as if set forth in its entirety; or a synthesized anionic form of the reaction product of (a) an aliphatic polyester of lactide, glycolide, epsilon-caprolactone, p-dioxanone, and trimethylene carbonate and (b) a poly(alkylene diglycolate) homopolymer or copolymer, as described in more detail in U.S. Pat. No. 5,644,002, the content of which is incorporated by reference as if set forth in its entirety.

Typical aliphatic lactone monomers that may be utilized to synthesize the anionic polyester described herein, and from which the repeat units of the anionic polyester are derived, are selected from the group consisting of glycolide, trimethylene carbonate, L-lactide, D-lactide, DL-lactide, mesolactide, epsilon-caprolactone, p-dioxanone, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

The organometallic catalysts include titanates and zirconates, or organotin compounds such as stannous chloride and stannous octoate.

The initiators are desirably compounds containing at least one anionic group, such as a carboxylic acid group, and at least one other group such as a hydroxyl group or an amine. Typical initiators, suitable for the synthesis of an anionic polyester having carboxylic acid groups, are alpha-hydroxyl acids such as glycolic acid, D-lactic acid, DL-Lactic acid, L-lactic acid; β-hydroxyacids, γ-hydroxyacids, δ-hydroxyacids, and ε-hydroxyacids such as ε-hydroxycaproic acid. Preferable initiators contain at least one carboxylic acid group and a primary hydroxyl group, such as glycolic acid. The alcohol group readily participates in a reaction that incorporates the initiator in the growing chain. Typical initiators suitable for the synthesis of branched polyesters with at least one carboxylic acid group are the polyhydroxyacids, such as glucoronic acid.

In certain forms, the anionic polyester may have only one carboxylic acid group. Such anionic polyesters are described in U.S. Pat. Nos. 4,201,216 and 4,994,074, the entire content which is incorporated herein by reference, and may be generally represented by the following formula:

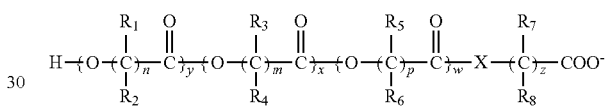

[A]

where 800≥x+y+w≥5; y≥0; x≥0; w≥0; n, m, p and z independently range from about 1 to about 12; $R_1$, $R_2$, $R_3$, $R_4$, $R_5$, $R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

The anionic polyesters include homopolymers and copolymers of lactide and glycolide, i.e., polylactide, polyglycolide, and copolymers of lactide and glycolide with each other and with other reactive monomers; poly(p-dioxanone); poly(alkylene oxalate); copolymers of vinyl acetates with unsaturated carboxylic acids such as crotonic, acrylic and methacrylic acids; and mixtures of such polymers. Particularly preferred polymers are the copolymers of lactide and glycolide, which contain from about 15 to 85% lactide, and have an inherent viscosity of from about 0.5 to 4.0 measured as a 0.1 percent solution in hexafluoroisopropanol at 25° C. These polymers are water-insoluble, rapidly absorbable, and soluble in many common organic solvents such as acetone, chloroform, toluene, xylene, and 1,1,2-trichloroethane.

It is also possible to produce other anionic polyesters in a similar fashion with terpolymers, tetramers, and the like, from building blocks including, but not limited to, glycolide, lactide, epsilon-caprolactone, trimethylene carbonate, and p-dioxanone.

Specific examples of such anionic polyesters are represented by formulae IA, IIA and IIIA.

The anionic polyester of Formula IA is a copolymer of epsilon-caprolactone and glycolide that is formed by using glycolic acid as an initiator and stannous octoate as the catalyst. The polymerization may be conducted in a batch process that allows the formation of a random copolymer. However, it is also possible to conduct the polymerization in such a way as to allow for the formation of a semi-block copolymer. The initiator ratio may be varied to allow one to obtain a molecular weight that makes the final copolymer in a useable form. The term "initiator ratio" as used herein, refers to the total moles of monomer divided by the total moles of initiator. For example, the initiator ratio may range from about 5 to about 600, corresponding to a Mn of about 575 to about 69,000, respectively. When the anionic polyester is used to prepare a coating on a substrate such as a medical device, the initiator ratio may range from about 10 to 30, corresponding to a Mn of about 1,150 to about 3,450, respectively. The size of the copolymer can vary greatly depending on its ultimate application.

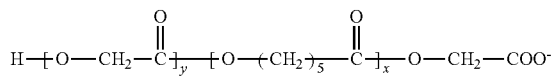
[IA]

wherein x ranges from about 5 to about 190; y ranges from about 5 to about 190; and x+y≤200

The anionic polyester represented by Formula IIA is a poly-(epsilon-caprolactone) that is polymerized with glycolic acid as an initiator, and is consequently terminated with a carboxylic acid group. For example, the initiator ratio may range from about 5 to about 600, corresponding to a Mn of about 575 to about 69,000, respectively. When the anionic polyester is used to prepare a coating on a substrate such as a medical device, the initiator ratio ranges from about 10 to about 30, corresponding to a Mn of about 1,150 to about 3,450, respectively.

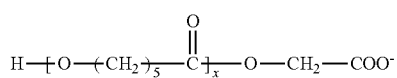
[IIA]

wherein x ranges from about 10 to about 200.

The anionic polyester represented by Formula IIIA is a copolymer formed from lactide and glycolide with glycolic acid as an initiator. The initiator ratio ranges from about 10 to about 200, which corresponds to a Mn of about 1,170 to about 28,800, respectively.

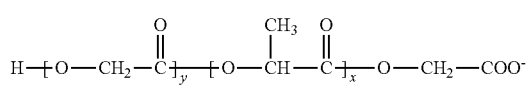
[IIIA]

wherein x ranges from about 5 to about 190; y ranges from about 5 to about 190; and x+y≤200.

Where the number of carboxylic acid groups is desirably 2 or more, one can provide an initiator that will cause the anionic polyester to form, for example, a branched structure. Examples of such initiators include, but are not limited to, tartaric acid, citric acid and the like. The branched structure may have one or more carboxylic acid groups in one or more branches on the polymer backbone or side chain. They may even be in the form of a dendrimer or star structure.

In an alternative form, the anionic polyester may have more than one carboxylic acid groups as represented by Formula A'. For example, copolymers of adipic acid and 1,4 butanediol disclosed in U.S. Pat. No. 3,942,532 may be synthesized in an anionic form as represented by Formula IVA', which is an anionic polyester that is rich in carboxylic acid groups and adipate.

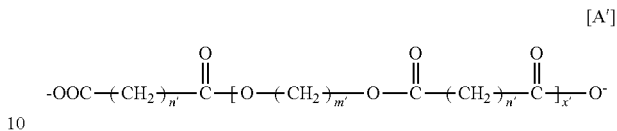
[A']

wherein 1≥n'≤13; 1≥m'≤9; and x' is the degree of polymerization and ranges from about 4 to about 50.

A specific example of such an anionic polyester is polytetramethylene adipate diacid represented by Formula IVA'.

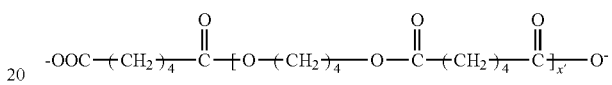

wherein x' ranges from about 4 to about 50. The value of x' depends on the molar ratio of diol to diacid and the extent of the conversion of the limiting reactant, where the molar ratio of the diol to the diacid is less than 1.

Examples of the diol that may be used to synthesize the anionic polyester of Formula IVA' include, but are not limited to, ethylene glycol, propylene glycol, butanediol, pentanediol, hexanediol, nonanediol, decanediol, undecanediol, dodecanediol, or mixtures thereof. Examples of the diacid include, but are not limited to, succinic, glutaric, adipic, pimelic, suberic, azelaic, sebacic acid, or mixtures thereof. The diols and diacids, upon reaction, may be condensed to obtain a polyester suitable for application as, for example, a substrate coating. Polyesters of the Formula A' may have a molecular weight in the range of approximately 200 to 10,200, or 1,000 to 15,000.

The antimicrobial cationic surfactant may be a monomeric amidoamine having at least one amide group and at least one amine group; wherein the amine group is either a primary amine, or a secondary amine, or a tertiary amine, or a quaternary amine, or a combination thereof. The following article may be referred to for further details concerning the synthesis of the amidoamines: Muzyczko, et al., "Fatty Amidoamine Derivatives: N,N-Dimethyl-N-(3-alkylamidopropyl)amines and Their Salts", Journal of the American Oil Chemists' Society, volume 45, number 11, pages 720-725 (1968). The entire contents of the above-cited article are hereby incorporated in the present specification by reference.

In one form, a portion of the amine groups are amidoamines, which comprise:

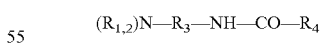

wherein:

$R_1$=H, Alkyl, Aryl, HO—$(CH_2CH_2$—O—$)_n$—, MeO—$(CH_2CH_2$—O—$)_n$, HO—$(CH_2)$n-;

$R_2$=H, Alkyl, Aryl, HO—$(CH_2CH_2$—O—$)_n$—, MeO—$(CH_2CH_2$—O—$)_n$—, HO—$(CH_2)$n-;

$R_3$=alkylene, arylene, —$(CH_2CH_2$—O—)—$(CH_2$—$)_n$;

$R_4$=Alkyl, Aryl, —$(CH_2CH_2$—O—)—$(CH_2$—$)_n$—$CH_3$, —O—$CH_3$, —O—$C_2H_5$, —O—$C_3H_7$; and n=1-30;

or the organic cation comprises:

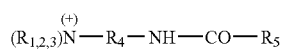

wherein:
$R_1$=H, Alkyl, Aryl, HO—(CH$_2$CH$_2$—O—)$_n$—, MeO—(CH$_2$CH$_2$—O—)$_n$—, HO—(CH$_2$)n-;
$R_2$=H, Alkyl, Aryl, HO—(CH$_2$CH$_2$—O—)$_n$—, MeO—(CH$_2$CH$_2$—O—)$_n$—, HO—(CH$_2$)n-;
$R_3$=H, Alkyl, Aryl;
$R_4$=alkylene, arylene, —(CH$_2$CH$_2$—O—)—(CH$_2$—)$_n$;
$R_5$=H, Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30.

In another form, the organic cation includes

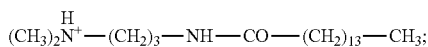

or

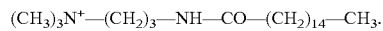

The complex of an anionic polyester and an antimicrobial cationic surfactant may be made by treating an anionic polyester with a solution of the source of the antimicrobial cationic surfactant. For example, the anionic polyester may be in the form of solid fibers, sheet, sponge or fabric. In certain forms, the anionic polyester is an ion exchanger. In other forms, the anionic polyester may be in free acid form, in which case for example, the source of the antimicrobial cationic surfactant may be a salt of a weak acid, whereby the anionic polyester is at least partially complexed by the antimicrobial cationic surfactant. When using an antimicrobial cationic surfactant, for example, the antimicrobial cationic surfactant is exchanged for a proton on the anionic polyester and part of the antimicrobial cationic surfactant is converted to a weak acid. The mixture of weak acid and salt in the solution results in a buffered solution which maintains a fairly constant pH and controls the degree of exchange reaction. An equilibrium reaction is established whereby the antimicrobial cationic surfactant is bound to the acid portion of the polyester and also to the salt molecules. Similar processes are described in EP-A-0437095, the entire content of which is expressly incorporated herein by reference.

The exchange reaction can be carried out in water or alcohol alone or carried out in mixtures of water and alcohols. The use of a mixture of water and alcohol provides good solubility for weak acid salts, and the alcohol enhances the ability of the anionic polyester to swell during the exchange reaction. Thus the physical properties (e.g. the inherent mechanical strength) of the anionic polyester are retained. Isopropyl alcohol is the preferred alcohol because many of the above-mentioned antimicrobial cationic surfactants have good solubility therein in combination with water. The alcohol to water molar ratio may be in the range of about 9:1 to 1:9. Linear and branched C$_2$-C$_{12}$ mono- or polyalcohols, including, but not limited to, n-propyl alcohol and ethanol, are suitable alcohols.

The amount of the antimicrobial cationic surfactant used is generally about equal to or up to twice the stoichiometric amount of carboxylic acid content of the polyester. Alternatively, a second charge of a stoichiometric amount of antimicrobial cationic surfactant can be used if the reaction is recharged with fresh solvent and salt after the first charge reaches a constant pH. The material with elevated pH is then washed to remove the excess antimicrobial cationic surfactants.

Disclosed herein is an antimicrobial composition comprising a complex of an anionic polyester with an antimicrobial cationic surfactant, wherein the complex comprises from about 5 wt. % to about 75 wt. % of the antimicrobial cationic surfactant, and or from about 10 wt. % to about 60 wt. % of antimicrobial cationic surfactant, or from about 20 wt. % to about 50 wt. % of antimicrobial cationic surfactant.

Accordingly, the complexes of the anionic polyesters previously described in Formulae A, A', and IA to IVA and the antimicrobial cationic surfactant, are represented by the following:

[B]
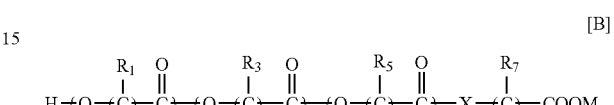

[IB]
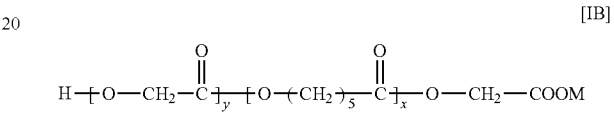

[IIB]
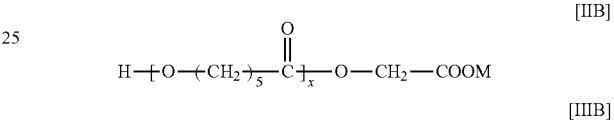

[IIIB]
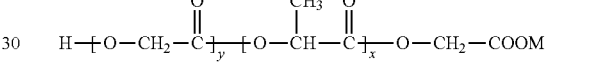

[B']
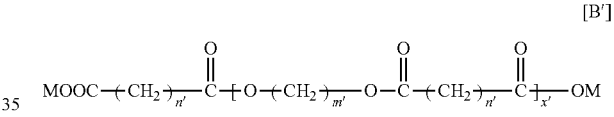

[IVB]
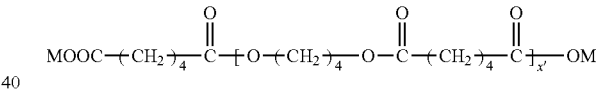

In a further aspect, the antimicrobial composition may optionally contain other components that improve the antimicrobial effectiveness of the composition, or that otherwise serve as active agents for other benefits. These components include, but are not limited to, additional antimicrobials, additional salts, any other excipients or active ingredients that provide the compositions with beneficial properties or enhance the antimicrobial activity of the compositions. Such components include, but are not limited to, antimicrobial agents such as triclosan, triclocarban, 2-phenoxyethanol, chlorhexidine salts, hexetidine and cetylpyridinium salts; antibiotics; and other active ingredients.

The antimicrobial compositions described herein may be used to coat substrate materials. Additionally, they can be a part of the coating that contains the antimicrobial composition described herein. These coatings may comprise either a single layer or multiple layers. In another form, the antimicrobial composition may also be applied to a preformed article or part of an article of manufacture as a coating. The coated article may be produced, for example, by dipping the article into the composition, coextruding the article, wire coating the article, or spraying the article with the composition and then drying the coated article.

The antimicrobial composition may be made separately, and then applied as a coating to a substrate such as a medical device. Alternatively, the antimicrobial composition may be made in situ, for example, by first coating a substrate such as a medical device with the anionic polyester followed by in situ treatment with a solubilized salt of the antimicrobial cationic surfactant, thus imparting antimicrobial properties to the substrate. Additionally, organic liquids such as organic solvents may be utilized to facilitate complexation of the antimicrobial cationic surfactant and the anionic polyester.

The antimicrobial compositions described herein are used alone or in combination with other polymer coatings to provide advantageous properties to the surface of the substrate. These compositions can also be used, to deliver pharmaceutical agents that, for example, are antiinfective, anticoagulants, improve healing, are antiviral, antifungal, antirombogenic or impart other properties to coated substrates.

The antimicrobial compositions are also used to inhibit algae, fungal, mollusk, or microbial growth on surfaces. The antimicrobial compositions described herein may also used as herbicides, insecticides, antifogging agents, diagnostic agents, screening agents, and antifoulants.

In another aspect, disclosed herein is an article of manufacture that is a medical device that comprises the antimicrobial compositions described herein. In one form, the antimicrobial composition can be used to form an article or a portion of the article, for example by spinning, molding, casting, or extrusion.

The antimicrobial composition can be utilized to manufacture a medical device including, but not limited to a fiber, mesh, powder, microspheres, flakes, sponge, foam, fabric, nonwoven, woven mat, a film, suture anchor device, suture, staple, surgical tack, clips, plate and screw, drug delivery device, adhesion prevention barrier, and tissue adhesive.

The medical device may be composed of one or more of the antimicrobial compositions disclosed herein, alone or in combination with other polymeric components.

As discussed above, the antimicrobial cationic surfactant may be incorporated into the anionic polyester in an aqueous alcohol environment. In one form, the antimicrobial cationic surfactant may be incorporated into the anionic polyester prior to forming a substrate such as a medical device. In an alternative form, the antimicrobial cationic surfactant can be incorporated into the anionic polyester after the formation of a substrate such as a medical device. For instance, the anionic polyester may be impregnated with the antimicrobial cationic surfactant by dipping, soaking, spraying or coating a medical device with the cationic surfactant dispersed in an aqueous alcohol environment, as shown in the Examples below.

Specific forms will now be described further, by way of example. While the following examples demonstrate certain forms disclosed herein, they are not to be interpreted as limiting the scope of the invention, but rather as contributing to a complete description.

EXAMPLES

Example 1

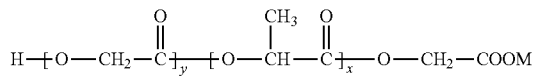

where

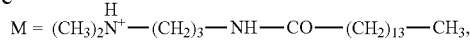

and may also comprise H⁺ depending on the relative stoichiometry of the acidic anionic polyester and the amidoamine.

A L(−) lactide/glycolide copolymer containing 65 mole % lactide and 35 mole % glycolide was synthesized with glycolic acid initiator using about 15 moles of monomers per mole of glycolic acid (initiator ratio 15), and with a 0.33 molar of stannous octoate catalyst to form the anionic polyester. The anionic polyester (0.54 grams) was dissolved in 5.4 grams of ethyl acetate forming solution A. Dimethylaminopropyl myristamide (Myristamidopropyl Dimethylamine or Schercodine M™ from Scher Chemicals Inc. of Clifton, N.J.) (0.081 grams) was dissolved in 5.4 grams of ethyl acetate forming solution B. Solutions A and B were admixed, to form the complex between the anionic polyester and the cationic dimethylaminopropyl myristamide cation.

To the above solution was added 0.54 grams of calcium stearate, which was then subjected to high shear to form a coating suspension. A 2/0 polyglactin 910 suture was coated by immersion. The remaining solvent was evaporated, yielding a suture with a coating loading of 4.63% by weight.

Antimicrobial efficacy was evaluated by an in vitro log reduction assay. A suture coated with the antimicrobial composition was challenged with approximately 10⁴ CFU bacteria by exposing five 3-cm sutures sample in a Petri dish to the inoculum for 60 minutes at room temperature. The inoculum was 10 µl of bacteria suspension in 20% serum/80% saline. The control was the same inoculum used in suture testing in a Petri dish without suture. After the microbial challenge, surviving bacteria from the suture samples and controls were enumerated by plate count. Tryptic soy agar containing the neutralizing agents Tween 80 and lecithin was used for the enumeration to eliminate the carry over antibacterial effect. Plates were incubated at 37° C. for 24 hours. Colonies were enumerated post-incubation. Log reduction was defined as the Log 10 CFU of the control (inoculum without suture)–Log 10 CFU of treated (inoculum with suture).

The resulting suture has good handling properties and a final concentration of 3200 ppm MAPD.

Example 2:

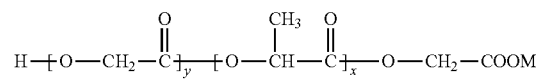

where

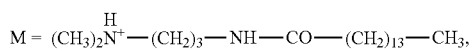

and may also comprise H⁺ depending on the relative stoichiometry of the acidic anionic polyester and the amidoamine.

A L(−) lactide/glycolide copolymer containing 65 mole % lactide and 35 mole % glycolide was synthesized with glycolic acid initiator using about 107.9 moles of monomers per mole of glycolic acid (initiator ratio 107.9), and with a 0.33 molar stannous octoate catalyst to form the anionic polyester.

The anionic polyester (0.54 grams) was dissolved in 5.4 grams of ethyl acetate forming solution A. Dimethylaminopropyl myristamide (0.081 grams) was dissolved in 5.4 grams of ethyl acetate forming solution B. Solutions A and B were admixed, to form the complex between the anionic polyester and the cationic dimethylaminopropyl myristamide cation.

To the above solution was added 0.54 grams of calcium stearate, which was then subjected to high shear to form a coating suspension. A 2/0 polyglactin 910 suture was coated by immersion. The remaining solvent was evaporated, yielding a suture with a coating loading of 5.98% by weight.

Antimicrobial efficacy was evaluated by an in vitro log reduction assay. A suture coated with the antimicrobial composition was challenged with approximately $10^4$ CFU bacteria by exposing five 3-cm sutures sample in a Petri dish to the inoculum for 60 minutes at room temperature. The inoculum was 10 µl of bacteria suspension in 20% serum/80% saline. The control was the same inoculum used in suture testing in a Petri dish without suture. After the microbial challenge, surviving bacteria from the suture samples and controls were enumerated by plate count. Tryptic soy agar containing the neutralizing agents Tween 80 and lecithin was used for the enumeration to eliminate the carry over antibacterial effect. Plates were incubated at 37° C. for 24 hours. Colonies were enumerated post-incubation. Log reduction was defined as the Log 10 CFU of the control (inoculum without suture) –Log 10 CFU of treated (inoculum with suture).

The resulting suture has good handling properties and a final concentration of 3200 ppm MAPD.

TABLE 1

Bacterial Log Reduction of examples 1 and 2 from 3 cm suture

| Copolymer initiator ratio | E. coli | S. aureus | P. aeruginosa |
|---|---|---|---|
| 15 | 2.5 | 2 | 1.8 |
| 107.9 | 2.3 | 1.4 | 0.9 |

Example 3

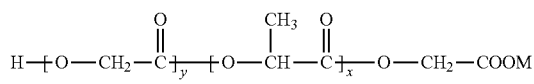

where $M=(CH_3)_3-N^+-(CH_2)_3-NH-CO-(CH_2)_{14}-CH_3$, and may also comprise $H^+$ depending on the relative stoichiometry of the acidic anionic polyester and the cationic quaternary amine.

A L(–) lactide/glycolide copolymer containing 65 mole % lactide and 35 mole % glycolide was synthesized with glycolic acid initiator using about 15 moles of monomers per mole of glycolic acid (initiator ratio 15), and with a 0.33 molar stannous octoate catalyst to form the anionic polyester.

The anionic polyester (0.54 grams) was dissolved in 10.8 grams of ethyl acetate forming solution A. Varisoft PATC (0.135 grams) obtained from Goldschmidt, Essen, Germany, which is a product that contains about 60% by weight of trimethyl(3-palmitoamidopropyl)ammonium chloride and about 40% by weight propyleneglycol was dissolved in 0.52 grams of ethanol, forming solution B. Solutions A and B were admixed, to form the complex between the anionic polyester and the cationic trimethyl(3-palmitoamidopropyl)ammonium ion.

To the above solution was added 0.54 grams of calcium stearate, which was then subjected to high shear to form a coating suspension. A 2/0 polyglactin 910 suture was coated by immersion. The remaining solvent was evaporated, yielding a suture with a coating loading of 5.2% by weight.

Antimicrobial efficacy was evaluated by an in vitro log reduction assay. A suture coated with the antimicrobial composition was challenged with approximately 104 CFU bacteria by exposing five 3-cm sutures sample in a Petri dish to the inoculum for 60 minutes at room temperature. The inoculum was 10 ul of bacteria suspension in 20% serum/80% saline. The control was the same inoculum used in suture testing in a Petri dish without suture. After the microbial challenge, surviving bacteria from the suture samples and controls were enumerated by plate count. Tryptic soy agar containing the neutralizing agents Tween 80 and lecithin was used for the enumeration to eliminate the carry over antibacterial effect. Plates were incubated at 37° C. for 24 hours. Colonies were enumerated post-incubation. Log reduction was defined as the Log 10 CFU of the control (inoculum without suture)–Log 10 CFU of treated (inoculum with suture).

The resulting suture has good handling properties and a final concentration of 3600 ppm MAPD.

Example 4

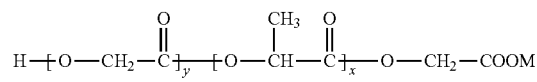

where $M=(CH_3)_3-N^+-(CH_2)_3-NH-CO-(CH_2)_{14}-CH_3$, and may also comprise $H^+$.

A L(–) lactide/glycolide copolymer containing 65 mole % lactide and 35 mole % glycolide was synthesized with glycolic acid initiator using about 107.9 moles of monomers per mole of glycolic acid (initiator ratio 107.9), and with a 0.33 molar stannous octoate catalyst to form the anionic polyester.

The anionic polyester (0.54 grams) was dissolved in 10.8 grams of ethyl acetate forming solution A. Varisoft PATC (0.135 grams) obtained from Goldschmidt, Essen, Germany, which is a product that contains about 60% by weight of trimethyl(3-palmitoamidopropyl)ammonium chloride and about 40% by weight propyleneglycol was dissolved in 0.52 grams of ethanol, forming solution B. Solutions A and B were admixed, to form the complex between the anionic polyester and the cationic trimethyl(3-palmitoamidopropyl)ammonium ion.

To the above solution was added 0.54 grams of calcium stearate, which was then subjected to high shear to form a coating suspension. A 2/0 polyglactin 910 suture was coated by immersion. The remaining solvent was evaporated, yielding a suture with a coating loading of 3.89% by weight.

Antimicrobial efficacy was evaluated by an in vitro log reduction assay. A suture coated with the antimicrobial composition was challenged with approximately 104 CFU bacteria by exposing five 3-cm sutures sample in a Petri dish to the inoculum for 60 minutes at room temperature. The inoculum was 10 µl of bacteria suspension in 20% serum/80% saline. The control was the same inoculum used in suture testing in a Petri dish without suture. After the microbial challenge, surviving bacteria from the suture samples and controls were enumerated by plate count. Tryptic soy agar containing the neutralizing agents Tween 80 and lecithin was used for the enumeration to eliminate the carry over antibacterial effect. Plates were incubated at 37° C. for 24 hours. Colonies were enumerated post-incubation. Log reduction was defined as the Log 10 CFU of the control (inoculum without suture)–Log 10 CFU of treated (inoculum with suture).

The resulting suture has good handling properties and a final concentration of 3600 ppm MAPD.

TABLE 2

| Bacterial Log Reduction of Examples 3 and 4 | | | |
|---|---|---|---|
| Copolymer initiator ratio | E. coli | S. aureus | P. aeruginosa |
| 15 | 2.8 | 2.5 | 1.9 |
| 107.9 | 2.7 | 2.3 | 1.8 |

While the subject invention has been illustrated and described in detail in the drawings and foregoing description, the disclosed forms are illustrative and not restrictive in character. All changes and modifications that come within the scope of the invention are desired to be protected.

What is claimed is:

1. An antimicrobial composition comprising:
a complex of an absorbable anionic polyester with a monomeric amidoamine or an organic cation, wherein the monomeric amidoamine comprises:

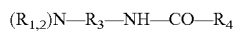

wherein:
$R_1$=H, Alkyl, Aryl, HO—(CH$_2$CH$_2$—O—)$_n$—, MeO—(CH$_2$CH$_2$—O—)$_n$—, HO—(CH$_2$)$_n$—;
$R_2$=H, Alkyl, Aryl, HO—(CH$_2$CH$_2$—O—)$_n$—, MeO—(CH$_2$CH$_2$—O—)$_n$—, HO—(CH$_2$)$_n$—;
$R_3$=alkylene, arylene, —(CH$_2$CH$_2$—O—)—(CH$_2$—)$_n$;
$R_4$=Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30; and
wherein the organic cation comprises:

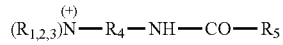

wherein:
$R_1$=H, Alkyl, Aryl, HO—(CH$_2$CH$_2$—O—)$_n$—, MeO—(CH$_2$CH$_2$—O—)$_n$—, HO—(CH$_2$)$_n$—;
$R_2$=H, Alkyl, Aryl, HO—(CH$_2$CH$_2$—O—)$_n$—, MeO—(CH$_2$CH$_2$—O—)$_n$—, HO—(CH$_2$)$_n$—;
$R_3$=H, Alkyl, Aryl;
$R_4$=alkylene, arylene, —(CH$_2$CH$_2$—O—)—(CH$_2$—)$_n$;
$R_5$=H, Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30;
wherein the anionic polyester is selected from the group consisting of an anionic polyester having at least one carboxylic group, a sulfonic acid polymer, and a phosphoric acid polymer, and at least one of $R_1$, $R_2$ and $R_3$ of the organic cation is H.

2. The antimicrobial composition according to claim 1, wherein the anionic polyester has the formula:

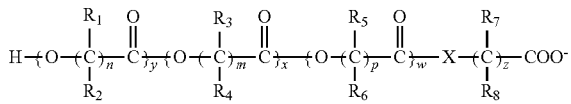

wherein 800≥x+y+w≥5; y≥0; x≥0; w≥0; n, m, p and z independently range from about 1 to about 12; $R_1$, $R_2$, $R_3$, $R_4$, $R_5$, $R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

3. The antimicrobial composition according to claim 2, wherein the anionic polyester is prepared from a ring-opening polymerization of an aliphatic lactone monomer which is polymerized in the presence of an organometallic catalyst and an anionic initiator.

4. The antimicrobial composition according to claim 3, wherein the aliphatic lactone monomer is selected from the group consisting of glycolide, trimethylene carbonate, L-lactide, D-lactide, DL-lactide, mesolactide, epsilon-caprolactone, p-dioxanone, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxepan-2-one, 1,5-dioxepan-2-one, 6,6-dimethyl-dioxepan-2-one, and 6,8-dioxabicycloctane-7-one.

5. The antimicrobial composition according to claim 3, wherein the anionic initiator is selected from the group consisting of alpha-hydroxyl acids, glycolic acid, D-lactic acid, DL-Lactic acid, L-lactic acid; β-hydroxyacids, γ-hydroxyacids, δ-hydroxyacids, ε-hydroxyacids, ε-hydroxycaproic acid, polyhydroxyacids, tartaric acid, citric acid and glucoronic acid.

6. The antimicrobial composition of claim 1, wherein greater than about 10% of the amine groups are organic cations.

7. The antimicrobial composition of claim 1, wherein the primary, secondary or tertiary amines are rendered into organic cations by protonation by reaction with an acidic anionic polyester.

8. The antimicrobial composition of claim 1, wherein the complex is formed with the anionic polyester and the organic cations.

9. The antimicrobial composition of claim 8, wherein the amount of antimicrobial cation in the complex is from about 5% to about 75% by weight based on the weight of the anionic polyester.

10. The antimicrobial composition of claim 1, wherein the organic cation is

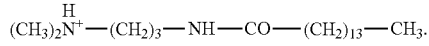

11. A medical device having an antimicrobial composition comprising:
a complex of an absorbable anionic polyester with a monomeric amidoamine or an organic cation, wherein the monomeric amidoamine comprises:

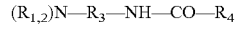

wherein:
$R_1$=H, Alkyl, Aryl, HO—(CH$_2$CH$_2$—O—)$_n$—, MeO—(CH$_2$CH$_2$—O—)$_n$—, HO—(CH$_2$)$_n$—;
$R_2$=H, Alkyl, Aryl, HO—(CH$_2$CH$_2$—O—)$_n$—, MeO—(CH$_2$CH$_2$—O—)$_n$—, HO—(CH$_2$)$_n$—;
$R_3$=alkylene, arylene, —(CH$_2$CH$_2$—O—)—(CH$_2$—)$_n$;
$R_4$=Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30; and
wherein the organic cation comprises:

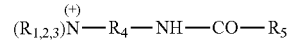

wherein:
R$_1$=H, Alkyl, Aryl, HO—(CH$_2$CH$_2$—O—)$_n$—, MeO—(CH$_2$CH$_2$—O—)$_n$—, HO—(CH$_2$)$_n$—;
R$_2$=H, Alkyl, Aryl, HO—(CH$_2$CH$_2$—O—)$_n$—, MeO—(CH$_2$CH$_2$—O—)$_n$—, HO—(CH$_2$)$_n$;
R$_3$=H, Alkyl, Aryl;
R$_4$=alkylene, arylene, —(CH$_2$CH$_2$—O—)—(CH$_2$—)$_n$;
R$_5$=H, Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30;
wherein the anionic polyester has at least one carboxylic acid group, and at least one of R$_1$, R$_2$ and R$_3$ of the organic cation is H.

12. The medical device according to claim 11, in the form of an implantable medical device.

13. The medical device according to claim 12, is in the form of a fiber, mesh, powder, microspheres, flakes, sponge, foam, fabric, nonwoven, woven mat, a film, suture anchor device, suture, catheter, staple, stent, surgical tack, clips, plate and screw, drug delivery device, adhesion prevention barrier, or tissue adhesive.

14. A method of making a complex of an absorbable anionic polyester with a monomeric amidoamine or an organic cation, wherein the monomeric amidoamine comprises:

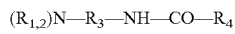
(R$_{1,2}$)N—R$_3$—NH—CO—R$_4$ wherein:
R$_1$=H, Alkyl, Aryl, HO—(CH$_2$CH$_2$—O—)$_n$—, MeO—(CH$_2$CH$_2$—O—)$_n$—, HO—(CH$_2$)$_n$—;
R$_2$=H, Alkyl, Aryl, HO—(CH$_2$CH$_2$—O—)$_n$—, MeO—(CH$_2$CH$_2$—O—)$_n$—, HO—(CH$_2$)$_n$—;
R$_3$=alkylene, arylene, —(CH$_2$CH$_2$—O—)—(CH$_2$—)$_n$;
R$_4$=Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30; and
wherein the organic cation comprises:

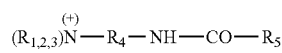
(R$_{1,2,3}$)N$^{(+)}$—R$_4$—NH—CO—R$_5$ wherein:
R$_1$=H, Alkyl, Aryl, HO—(CH$_2$CH$_2$—O—)$_n$—, MeO—(CH$_2$CH$_2$—O—)$_n$—, HO—(CH$_2$)$_n$—;
R$_2$=H, Alkyl, Aryl, HO—(CH$_2$CH$_2$—O—)$_n$—, MeO—(CH$_2$CH$_2$—O—)$_n$—, HO—(CH$_2$)$_n$—;
R$_3$=H, Alkyl, Aryl;
R$_4$=alkylene, arylene, —(CH$_2$CH$_2$—O—)—(CH$_2$—)$_n$;
R$_5$=H, Alkyl, Aryl, —(CH$_2$CH$_2$—O—)—(CH$_2$—)$_n$—CH$_3$, —O—CH$_3$, —O—C$_2$H$_5$, —O—C$_3$H$_7$; and
n=1-30; and
the anionic polyester has at least one carboxylic acid group, and at least one of R$_1$, R$_2$ and R$_3$ of the organic cation is H, comprising the step of incorporating an effective amount of the monomeric amidoamine or the organic cation with the anionic polyester having at least one carboxylic acid group in an aqueous soluble alcohol.

15. The method according to claim 14, wherein the anionic polyester has the formula:

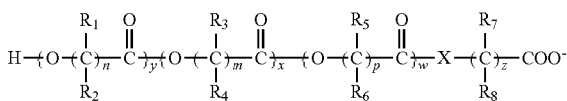

wherein 800≥x+y+w≥5; y≥0; x≥0; w≥0; n, m, p and z independently range from about 1 to about 12; R$_1$, R$_2$, R$_3$, R$_4$, R$_5$, R$_6$ are independently H or a linear or branched alkyl group having from about 1 to about 12 carbon atoms; X is either —O— or —NH—; and R$_7$ and R$_8$ are independently H, a linear or branched alkyl group having from about 1 to about 12 carbon atoms, or a —COOH group.

16. An antimicrobial composition of an absorbable anionic polyester and an organic cation comprising the following formula:

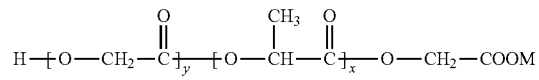

wherein:
x+y ranges from about 5 to about 300 and M is

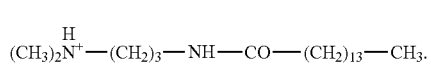
(CH$_3$)$_2$N$^+$H—(CH$_2$)$_3$—NH—CO—(CH$_2$)$_{13}$—CH$_3$.

* * * * *